United States Patent

Witzel et al.

Patent Number: 5,557,011
Date of Patent: Sep. 17, 1996

[54] PREPARATION OF DIAMINES

[75] Inventors: Tom Witzel; Eberhard Fuchs, both of Ludwigshafen, Germany

[73] Assignee: BASF Aktiengesellschaft, Ludwigshafen, Germany

[21] Appl. No.: 339,916

[22] Filed: Nov. 15, 1994

Related U.S. Application Data

[63] Continuation of Ser. No. 150,364, Nov. 9, 1993, abandoned.

[30] Foreign Application Priority Data

Nov. 26, 1992 [DE] Germany .......................... 42 39 782.0

[51] Int. Cl.$^6$ .................................. C07C 209/48
[52] U.S. Cl. ..................... 564/492; 564/491; 564/469; 564/470
[58] Field of Search .................. 564/491, 469, 564/470, 492

[56] References Cited

U.S. PATENT DOCUMENTS

| | | | |
|---|---|---|---|
| 2,166,183 | 7/1939 | Signaigo | 564/490 |
| 3,673,251 | 6/1972 | Frampton et al. | 564/491 |
| 5,101,075 | 3/1992 | Käsbauer et al. | 564/490 |
| 5,239,120 | 8/1993 | Merger et al. | 564/491 |

FOREIGN PATENT DOCUMENTS

| | | |
|---|---|---|
| 3935641 | 5/1991 | Germany . |
| 1157637 | 7/1969 | United Kingdom . |
| 1157638 | 7/1969 | United Kingdom . |
| 1157639 | 7/1969 | United Kingdom . |

OTHER PUBLICATIONS

Studies in Surface Science and Catalysis, vol. 27 (1986), pp. 105–144.
Ind. Tech. Bull., vol. 11 (1970) pp. 19–24.
Catalysis of Organic Reactions, Marcel Dekker (1992) p. 103.

*Primary Examiner*—Brian Burn
*Attorney, Agent, or Firm*—John H. Shurtleff

[57] ABSTRACT

Process for the preparation of diamines of the general formula I

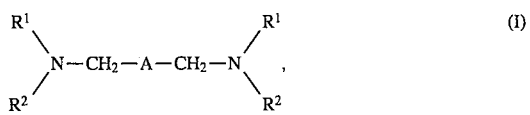

in which
A denotes a $C_1$–$C_{20}$ alkylene chain optionally mono- to penta-substituted by $C_1$–$C_4$ alkyl,
$R^1$, $R^2$ denote $C_1$–$C_{20}$ alkyl, $C_1$–$C_{20}$ hydroxyalkyl, $C_3$–$C_8$ cycloalkyl, $C_4$–$C_{20}$ alkylcycloalkyl, $C_4$–$C_{20}$ cycloalkylalkyl, phenyl, $C_7$–$C_{20}$ phenylalkyl, $C_1$–$C_{20}$ alkoxyalkyl, $C_7$–$C_{20}$ phenoxyalkyl or together a saturated or unsaturated $C_2$–$C_6$ alkylene chain optionally monosubstituted, disubstituted, or trisubstituted by $C_1$–$C_4$ alkyl and optionally interrupted by oxygen or nitrogen,
by the reaction of dinitriles of the general formula II $$NC-A-CN \qquad (II),$$

in which A has the aforementioned meaning,
with secondary amines of the general formula II

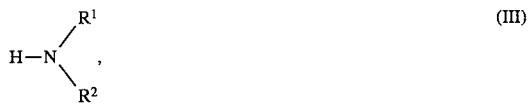

in which $R^1$ and $R^2$ have the aforementioned meanings,
with hydrogen at temperatures ranging from 50° to 200° C. and pressures ranging from 5 to 300 bar in the presence of a hydrogenation catalyst, in which a palladium catalyst on an oxidic support is used as hydrogenation catalyst.

10 Claims, No Drawings

PREPARATION OF DIAMINES

This application is a continuation of application Ser. No. 08/150,364, filed Nov. 9, 1993 (abandoned).

The present invention relates to a process for the preparation of diamines from dinitriles and secondary amines over a palladium catalyst at elevated temperatures and pressures.

*Stud. Surf. Sci. Catal.* 27, (1986) 105 to 144 describes on page 123 the synthesis of tertiary amines from secondary amines and an aliphatic nitrile over a Pd/C catalyst, the process is encumbered, however, with the drawback that the reaction rate decreases with rising starting concentration of the secondary amine, and only an unsatisfactory yield is achieved.

Moreover, *Ind. Tech. Bull.* 11, (1970) 19 to 24 reports that the synthesis of tertiary amines from a secondary amine and a nitrile cannot be expected to take place in a commercially useful yield. Although the tertiary amine does form tripentylamine from valeronitrile over Pd/C at a selectivity of 84%, the conversion rate achieved is only an unsatisfactory 28%. On the other hand, the secondary butylpentylamine is obtained from valeronitrile and butylamine over the same catalyst at a selectivity of 93%, the yield being 54%. No tertiary amine is formed despite the presence of secondary amine however.

*Catalysis of Organic Reactions*, Marcel Dekker, New York, Basel 1992, page 103, recommends the use of catalyst supports such as aluminum oxide for the preparation of primary amines, since the acid centers of the support adsorb the amine already formed at sites remote from he active centers, and thus prevent linkages.

GB-A 1,157,637, GB-A 1,157,638 and GB-A 1,157,639 reveal the reaction of 2-methylglutarodinitrile with diethylamine in the presence of hydrogen and palladium on barium sulfate or preferably palladium on carbon to form 5-diethylamino-2-methylvaleronitrile. No tetraethyl derivative was found despite the long reaction time and a diethylamine excess of 200 mol %, although the diethylamino group reacts not only with the nitrile groups in position 5, but also with those in position 1 (ratio: 4 to 1).

DE-A 3,935,641 describes the synthesis of a secondary amine over a palladium catalyst. In this case dimethylaminopropionitrile is caused to react with itself under hydrogenation conditions to produce bis(3-dimethylaminopropyl)-amine. The formation of a tertiary amine can only be achieved using a spinel which is far more expensive to manufacture than support material, the yield being not more than 58%.

U.S. Pat. No. 2,166,183 warns against the formation of cyclic secondary amines in the hydrogenation of dinitriles having 4, 5, or 6 carbon atoms; ie against the formation of hexamethyleneimine in the case of adipodinitrile.

It is thus an object of the present invention to overcome the aforementioned drawbacks.

Accordingly, we have now found a novel and improved process for the preparation of a diamine of the general formula I

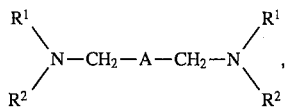   (I)

in which
A denotes a $C_1$–$C_{20}$ alkylene chain optionally mono- to penta-substituted by $C_1$–$C_4$ alkyl, $R^1$, $R^2$ denote $C_1$–$C_{20}$ alkyl, $C_1$–$C_{20}$ hydroxyalkyl, $C_3$–$C_8$ cycloalkyl, $C_4$–$C_{20}$ alkylcycloalkyl, $C_4$–$C_{20}$ cycloalkylalkyl, phenyl, $C_7$–$C_{20}$ phenylalkyl, $C_1$–$C_{20}$ alkoxyalkyl, $C_7$–$C_{20}$ phenoxyalkyl or together a saturated or unsaturated $C_2$–$C_8$ alkylene chain optionally monosubstituted, disubstituted, or trisubstituted by $C_1$–$C_4$ alkyl and optionally interrupted by oxygen or nitrogen, by the reaction of dinitriles of the general formula II

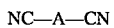   (II), in which A has the aforementioned meaning,
with secondary amines of the general formula III

   (III)

in which $R^1$ and $R^2$ have the aforementioned meanings, using hydrogen at temperatures ranging from 50° to 200° C. and pressures ranging from 5 to 300 bar in the presence of a hydrogenation catalyst, wherein a palladium catalyst on an oxidic support is used as hydrogenation catalyst.

The process of the invention can be carried out as follows:

The reaction of dinitriles of the formula II with the diamines of formula III using hydrogen may be carried out at temperatures ranging from 50° to 200° C. and preferably from 90° to 170° C. and more preferably from 120° to 160° C. and pressures ranging from 5 to 300 bar and preferably from 50 to 200 bar and more preferably from 70 to 150 bar batchwise or, preferably, continuously in pressure apparatus such as autoclaves or preferably in a tubular reactor over specific hydrogenation catalysts.

Suitable hydrogenation catalysts are palladium catalysts on oxidic supports. Examples of suitable oxidic supports are $\gamma$-$Al_2O_3$, $SiO_2$, $TiO_2$, $ZrO_2$, or $Al_2O_3$, $SiO_2$, $TiO_2$, or $ZrO_2$ doped with alkali metal oxide or alkaline-earth metal oxide.

These palladium catalysts usually contain from 0.1 to 10 wt. % and preferably from 0.3 to 5 wt. % and more preferably from 0.5 to 1 wt. % of palladium, based on the total weight of the catalyst.

The palladium catalysts are well known, or can be prepared by processes generally known in the art, for example, by impregnating the support with palladium compounds such as $PdCl_2$ or $Pd(NO_3)_2$.

The molar ratio of secondary amine III to nitrile II is usually from 2:1 to 30:1 and preferably from 3:1 to 10:1 and more preferably from 4:1 to 8:1.

The diamines I produced by the process of the invention may be purified in known manner, e.g. by distillation.

The connecting member A and the substituents $R^1$ and $R^2$ in the compounds I, II and III have the following meanings:

A
   a $C_1$–$C_{20}$ alkylene chain optionally mono- to penta-substituted by $C_1$–$C_4$ alkyl such as —($CH_2$)—, —($CH_2$)$_2$—, —($CH_2$)$_3$—, —($CH_2$)$_4$—, —($CH_2$)$_5$—, —($CH_2$)$_6$—, —($CH_2$)$_7$—, —($CH_2$)$_8$—, —($CH_2$)$_9$—, —($CH_2$)$_{10}$—, —($CH_2$)$_{11}$—, —($CH_2$)$_{12}$—, —($CH_2$)$_{13}$—, —($CH_2$)$_{14}$—, —($CH_2$)$_{15}$—, —($CH_2$)$_{16}$—, —($CH_2$)$_{17}$—, —($CH_2$)$_{18}$—, —($CH_2$)$_{19}$—, —($CH_2$)$_{20}$—, —$CH(CH_3)$—$CH_2$—$CH_2$—, —$CH_2$—$CH(CH_3)$—$CH_2$—, and —$CH_2$—$C(CH_3)_2$—$CH_2$— and preferably —($CH_2$)—, —($CH_2$)$_2$—, —($CH_2$)$_3$—, —($CH_2$)$_4$—, —($CH_2$)$_6$—, —$CH_2$—$CH(CH_3)$—$CH_2$—$CH_2$—, —$CH_2$—$C(CH_2)$—$CH_2$—$CH_2$ —$CH_2$—$CH_2$—$CH(CN)$—$CH_2$—$CH_2$—$CH_2$ and more preferably —($CH_2$)$_4$—

$R^1$, $R^2$ $C_1$–$C_{20}$ alkyl and preferably $C_1$–$C_{12}$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, n-nonyl, isononyl, n-decyl, isodecyl, n-undecyl, isoundecyl, n-dodecyl, and isododecyl and more preferably $C_1$–$C_4$ alkyl such as methyl, ethyl, n-propyl, isopropyl, n-butyl, isobutyl, sec-butyl, and ten-butyl, $C_1$–$C_{20}$ hydroxyalkyl and preferably $C_2$–$C_8$ hydroxy-n-alkyl such as 2-hydroxyethyl, 2-hydroxy-n-propyl, and 3-hydroxy-n-propyl, $C_3$–$C_8$ cycloalkyl such as cyclopropyl, cyclobutyl, cyclopentyl, cyclohexyl, cycloheptyl, and cyclooctyl and preferably cyclopentyl, cyclohexyl, and cyclooctyl and more preferably cyclopentyl and cyclohexyl, $C_4$–$C_{20}$ alkylcycloalkyl and preferably $C_4$–$C_{12}$ alkylcycloalkyl, $C_4$–$C_{20}$ cycloalkylalkyl and preferably $C_4$–$C_{12}$ cycloalkyl alkyl, phenyl, $C_7$–$C_{20}$ phenylalkyl and preferably $C_7$–$C_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl, and 4-phenylbutyl and more preferably benzyl, 1-phenethyl, and 2-phenethyl, $C_2$–$C_{20}$ alkoxyalkyl and preferably $C_2$–$C_8$ alkoxyalkyl such as methoxymethyl, 2-methoxyethyl, 2-ethoxyethyl, 3-methoxypropyl, and 3-ethoxypropyl, $C_7$–$C_{20}$ phenoxyalkyl and preferably $C_7$–$C_{12}$ phenoxyalkyl such as 2-phenoxyethyl, 2-phenoxypropyl, 3-phenoxypropyl, 2-phenoxybutyl, 3-phenoxybutyl, and 4-phenoxybutyl and more preferably 2-phenoxyethyl, $R^1$, $R^2$ together form a $C_2$–$C_6$ alkylene, optionally monosubstituted, disubstituted, or trisubstituted by $C_1$–$C_4$ alkyl such as —$(CH_2)_2$—, —$(CH_2)_3$—, —$(CH_2)_4$—, —$(CH_2)_5$—, —$(CH_2)_6$—, —$CH(CH_3)$—$CH_2$—$CH_2$—, and —$CH_2$—$CH(CH_3)$—$CH_2$—, a $C_2$–$C_6$ alkylene interrupted by oxygen and/or nitrogen and optionally substituted by $C_1$–$C_4$ alkyl such as —$CH_2$—$CH_2$—O—$CH_2$—$CH_2$, —$CH_2$—$CH_2$—NH—$CH_2$—$CH_2$—$CH_2$—$CH_2$—$N(CH_3)$—$CH_2$—$CH_2$—, $CH_2$—$CH_2$—$N(CH_2CH_3)$—$CH_2$—$CH_2$—, and —$CH_2$—$CH(CH_3)$—O—$CH(CH_3)$—$CH_2$ Suberic dinitrile, adipodinitrile, methylglutarodinitrile, methyleneglutarodinitrile, glutarodinitrile, succinodinitrile, malonic dinitrile, 1,3,6-tricyanohexane and preferably adipodinitrile.

Dimethylamine, diethylamine, dipropylamine, diisopropylamine, di-n-butylamine, diisobutylamine, di-sec-butylamine, di-2-ethylhexyl amine, di-tridecylamine, dicyclohexylamine, ethyl-methylamine, methyl cylohexylamine, ethyl-cyclohexylamine, pyrrolidine, piperidine, piperazine, morpholine, diphenylamine, n-methylaniline, n-ethylaniline, diethanolamine, diisopropanolamine, di-2-methoxyethylamine, di-2-ethoxyethylamine, methylethanolamine, ethylethanolamine, isopropylethanolamine, and hydroxyethylaniline and more preferably dimethylamine.

Thus N,N,N',N'-tetramethylhexamethylenediamine is particularly preferred as diamine I.

These tertiary amines are curing agents for epoxy resins, catalysts for polyurethanes, intermediates for the preparation of quaternary ammonium compounds, plasticizers, anticorrosive agents, textile auxiliaries, and emulsifiers.

EXAMPLES

| Catalyst A: 4% | of Pd on $Al_2O_3$ |
| Catalyst B: 0.5% | of Pd on $Al_2O_3$ with 20% of CaO |
| Catalyst C: 1% | of Pd on $Al_2O_3$ with 20% of MgO |
| Catalyst D: 0.5% | of Pd; 5% of Pr on $Al_2O_3$ |

Example 1

10 g of adipodinitrile were hydrogenated in an autoclave with 120 mL of dimethylamine (molar ratio: 1 to 20) over 1 g of commercial palladium on aluminum oxide (palladium content 5%) acting as catalyst over a period of 10 h at a temperature of 100° C. and a pressure of 200 bar. There were obtained 12.7 g (80%) of tetramethylhexamethylenediamine (conversion 100%; selectivity 80%).

Example 2

100 g of adipodinitrile were hydrogenated in an autoclave with 1270 mL of dimethylamine over 40 g of catalyst D over a period of 27 h at a temperature of 150° C. and a pressure of 80 bar. The effluent contained 12.7 g (80%) of tetramethylhexamethylenediamine, the yield being quantitative.

Example 3

8.1 mL/h of adipodinitrile and 43 mL/h of liquid dimethylamine (molar ratio: 1 to 5) were pumped through a vertical hydrogenation reactor (diameter: 16 mm; packed with 28 g of catalyst A to a height of 600 mm; oil-heated double-walled jacket)in a liquid phase process carried out under a pressure of 80 bar and at a temperature of 150° C. L/h (STP) of hydrogen were passed simultaneously upwardly through the reactor. The pressure was let down to atmospheric and excess dimethylamine was distilled off and the hydrogenated effluent analyzed by quantitative gas chromatography. There were obtained 11 g/h (86%) of tetramethylhexamethylenediamine.

Example 4

Using the apparatus described in Example 3 16.7 g/h (93%) of tetramethylhexamethylenediamine were obtained from 11.3 mL/h Of adipodinitrile and 34 mL/h of dimethylamine (molar ratio: 1 to 5) over 43 g of catalyst B under a pressure of 80 bar and at a temperature of 150° C.

Example 5

Using the apparatus described in Example 3 15.7 g/h (94%) of tetramethylhexamethylenediamine were obtained from 10.5 mL/h of adipodinitrile and 32 mL/h of dimethylamine (molar ratio: 1 to 5) over 40 g of catalyst C under a pressure of 80 bar and at a temperature of 150° C.

Example 6

Using the apparatus described in Example 3 12.7 g (93%) of tetramethylhexamethylenediamine were obtained from 8.2 mL/h of adipodinitrile and 25 mL/h of dimethylamine (molar ratio: 1 to 5) over 39 g of catalyst D under a pressure of 80 bar and at a temperature of 155° C.

We claim:

1. A process for the preparation of a tertiary diamine of the formula

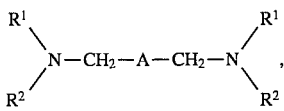

in which A denotes a $C_1$–$C_{20}$ alkylene chain optionally mono- to penta-substituted by $C_1$–$C_4$-alkyl, and $R^1$ and $R^2$ each denote $C_1$–$C_{20}$-alkyl, $C_1$–$C_{20}$-hydroxyalkyl, $C_3$–$C_8$-cycloalkyl, $C_4$–$C_{20}$-alkylcycloalkyl, $C_4$–$C_{20}$-cycloalkylalkyl, phenyl, $C_7$–$C_{20}$-phenylalkyl, $C_1$–$C_{20}$-alkoxyalkyl, $C_7$–$C_{20}$-phenoxyalkyl, or when taken together, $R^1$ and $R^2$ denote a saturated or unsaturated $C_2$–$C_6$-alkylene chain optionally substituted by $C_1$–$C_4$-alkyl and optionally interrupted by oxygen or nitrogen, said process comprising:

reacting a dinitrile of the formula

in which A has the aforementioned meaning, and a secondary amine of the formula

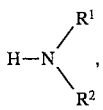

in which $R^1$ and $R^2$ have the aforementioned meanings, with hydrogen at temperatures ranging from 50° to 200° C. and pressures ranging from 5 to 300 bar in the presence of palladium supported on an oxide selected from the group consisting of $\gamma$-$AlO_2O_3$, $SiO_2$, $TiO_2$ or $ZrO_2$ or on said oxide doped with an alkali metal oxide or alkaline-earth metal oxide, as a hydrogenation catalyst.

2. A process as claimed in claim 1 wherein the reaction is carried out at a temperature of from 90° to 170° C. and a pressure of from 50 to 200 bar.

3. A process as claimed in claim 1 wherein the reaction is carried out at a temperature of from 120° to 160° C. and a pressure of from 70 to 150 bar.

4. A process as claimed in claim 1 wherein the reaction is carried out with a molar ratio of the secondary amine III to the dinitrile II of 2:1 to 30:1.

5. A process as claimed in claim 1 wherein the reaction is carried out with a molar ratio of the secondary amine III to the dinitrile II of 3:1 to 10:1.

6. A process as claimed in claim 1 wherein the reaction is carried out with a molar ratio of the secondary amine III to the dinitrile II of 4:1 to 8:1.

7. A process as claimed in claim 1 wherein the reaction is carried out at a temperature of from 90° to 170° C., a pressure of from 50 to 200 bar and with a molar ratio of the secondary amine III to the dinitrile II of 3:1 to 10:1.

8. A process as claimed in claim 1 wherein the support is $\gamma$-$Al_2O_3$ containing 0.1 to 10% palladium, based on the total weight of the catalyst.

9. A process as claimed in claim 1 wherein the support is $\gamma$-$Al_2O_3$ containing 0.3 to 5% palladium, based on the total weight of the catalyst.

10. A process as claimed in claim 1 wherein the dinitrile is adiponitrile and the secondary diamine III is dimethylamine.

* * * * *

UNITED STATES PATENT AND TRADEMARK OFFICE
CERTIFICATE OF CORRECTION

PATENT NO. : 5,557,011
DATED : Sep. 17, 1996
INVENTOR(S) : Tom Witzel, Eberhard Fuchs It is certified that error appears in the above-indentified patent and that said Letters Patent is hereby corrected as shown below:

IN THE ABSTRACT, just before the space occupied by the structural formula (III), in the line which reads:

"with secondary amines of the general formula II", cancel "II" and substitute -- III --.

Signed and Sealed this

Fifth Day of August, 1997

*Attest:*

BRUCE LEHMAN

*Attesting Officer*     *Commissioner of Patents and Trademarks*